US006139567A

United States Patent [19]

McCarty et al.

[11] Patent Number: 6,139,567

[45] Date of Patent: Oct. 31, 2000

[54] BOX SEAT

[76] Inventors: Elizabeth A. McCarty, 922 S. Kenilworth Ave., Oak Park, Ill. 60304; Michael P. Erzen, 5224 W. Warner, Chicago, Ill. 60641

[21] Appl. No.: 09/057,828

[22] Filed: Apr. 9, 1998

Related U.S. Application Data

[60] Provisional application No. 60/043,129, Apr. 9, 1997.

[51] Int. Cl.$^{7}$ .......... A61F 05/00

[52] U.S. Cl. .......... 606/237; 5/633

[58] Field of Search .......... 606/237, 240, 606/241, 245, 238; 682/145, 907, 910; 190/107, 8, 30, 31, 32; 297/188.08, 188.13, 220, 221; 5/633, 634

[56] References Cited

U.S. PATENT DOCUMENTS 309,678 12/1884 Aubin .
969,099 8/1910 Fuchs .
1,004,630 10/1911 Cotter .......... 297/220
1,103,730 7/1914 Anderson .
2,368,436 1/1945 Williams .
2,429,795 10/1947 Blanchard et al. .
2,777,138 1/1957 Gallagher .......... 5/634
2,802,220 8/1957 Locke .......... 5/632
2,884,991 5/1959 Bloomquist .
3,276,817 10/1966 Marple .
3,565,419 2/1971 Allard et al. .
4,927,211 5/1990 Bolcerek .......... 297/465
5,416,939 5/1995 Maalouli .
5,556,120 9/1996 Davis .......... 280/304.1
5,730,688 3/1998 Prusick .......... 482/130
5,740,567 4/1998 Mitchell .......... 5/420
5,882,079 3/1999 Yang .......... 297/377
5,987,675 11/1999 Kim .......... 5/632

*Primary Examiner*—Justine R. Yu
*Attorney, Agent, or Firm*—Olson & Hierl, Ltd.

[57] ABSTRACT

A box seat provides for selected angular adjustment of a seat back, the seat back being collapsible into the seat base, thereby defining a closed container of compact configuration adapted to retain accessories for use with the box seat.

3 Claims, 5 Drawing Sheets

BOX SEAT

PRIORITY

This patent application is based on Provisional Patent Application Ser. No. 60/043,129, filed Apr. 9, 1997.

BACKGROUND OF THE INVENTION

Field of the Invention

The box seat is a positioning device to be used for therapeutic intervention and evaluation. This apparatus is designed to be used in conjunction with physical therapy and not as a permanent seating apparatus. Used correctly, this device will assists therapists by properly and safely positioning their patients during therapeutic intervention. The box seat was designed to be used on mat tables, patients beds, or on the floor. Once the patient is properly positioned, the therapist can work hands free on isolated tasks. Complex patients that often require two therapists to handle will only require one and will enhance valuable therapy time.

Occupational therapists and rehabilitation engineers are often frustrated working with patients on mat tables that do not provide positioning options. The box seat is designed to enhance treatment sessions by providing a supportive surface for the patient.

The box seat offers a variety of positioning angles, lumbar and lateral supports, head support, and pelvic position strap and wedges for optimal spinal alignment. Also included are documentation forms to mark the patients therapeutic progress, goniometer's, wheelchair assessment forms, an easy guide to selecting appropriate seating systems, and a video tape to provided guided instructions as to the use of the box seat.

This device works in numerous settings and with a variety of diagnoses both adults and pediatrics. From the rehab gym to the home health patient, positive therapeutic results can be obtained by helping patients maintain correct posture and trunk stability. The ability to be set to a variety of positions assists with the evaluation process and helps the therapist to choose appropriate accessories, included with the seat, for the particular needs. Importantly, the patient also feels more secure when positioned properly and more inclined or able to participate in a treatment session.

This product can be used with adult, geriatric and pediatric patients. It can be used with a variety of diagnoses including but not limited to; spinal cord injury, traumatic brain injury, multiple sclerosis, amputees, cerebral vascular accidents, cerebral palsy, arthritis and general debility. This product can be used in a variety of settings such as acute hospitals, rehabilitation hospitals, assisted living, nursing homes, home health, and for private home use.

The therapy kit, integral with the box seat includes: one (1) lateral support strapping system; one (1) removable head rest; one (1) lumbar roll; one (1) demonstration video; one (1) measuring tape; one (1) packet of treatment documentation guidelines; and one (1) piece of non-slip material to be used under the patient.

DESCRIPTION OF RELATED ART

Known products on the market are limited to specific angles or are cumbersome to use and store, such as in a crowded gym, therapy office, or examination room. They are not easily transportable for home therapy sessions.

SUMMARY OF INVENTION

The box seat is a positioning device to be used for therapeutic intervention and evaluation This apparatus is designed to be used in conjunction with therapy and not as a permanent seating apparatus. Used correctly, this device will assist therapists by properly and safely positioning their patients during therapeutic intervention. This product, constructed of wood, has a unique wedge or triangular design. This design facilitates a surface that can be adjusted from a horizontal position of 20 degrees up to a vertical 90 degrees. This product offers accessory items including lateral, head and lumbar supports to provide optimal postural alignment. The box seat was designed to be used on mat tables, beds, or on the floor. The accessory items are stored within the box seat and the apparatus is portable and easy to use.

BRIEF DESCRIPTION OF DRAWINGS

The following drawings, in which like reference characters indicate like parts, are illustrative of embodiments of the invention and are not intended to limit the scope of the invention in any manner whatsoever, as encompassed by the claims forming a part hereof.

DETAILED DESCRIPTION OF PREFERRED EMBODIMENT

Figure 1:
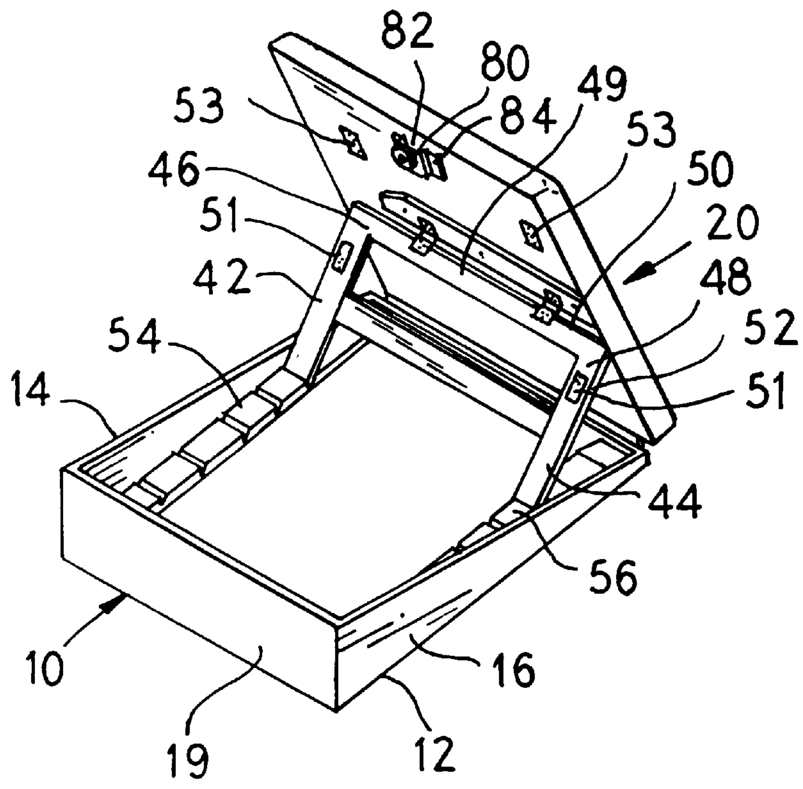
FIG. 1 is a perspective view of the box seat.
Figure 2:
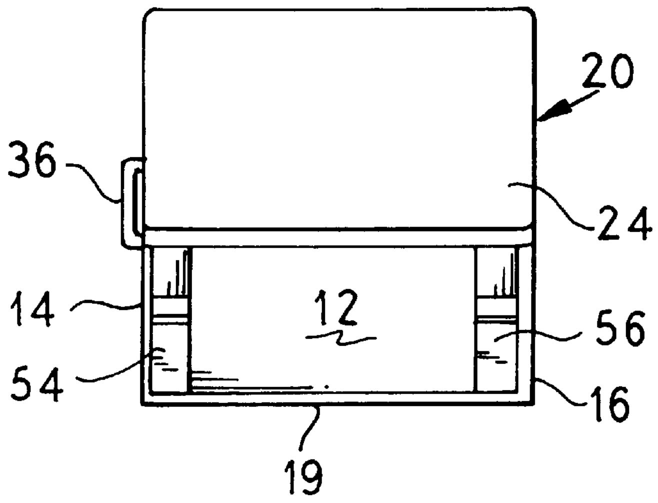
FIG. 2 is a sectional view of the box seat lid/seat back unit.
Figure 3:
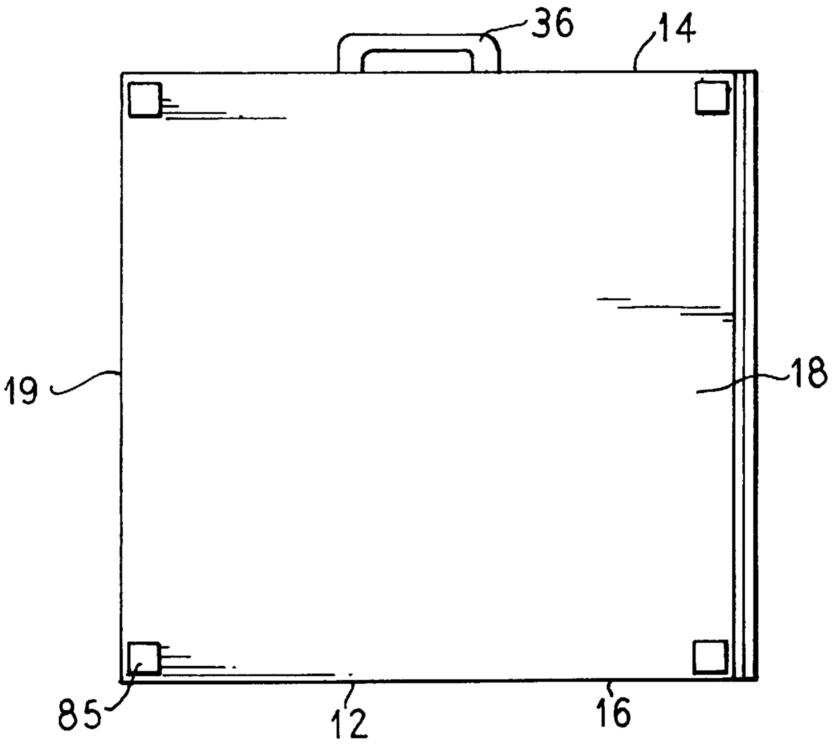
FIG. 3 is a bottom plan view of the box seat.
Figure 4:
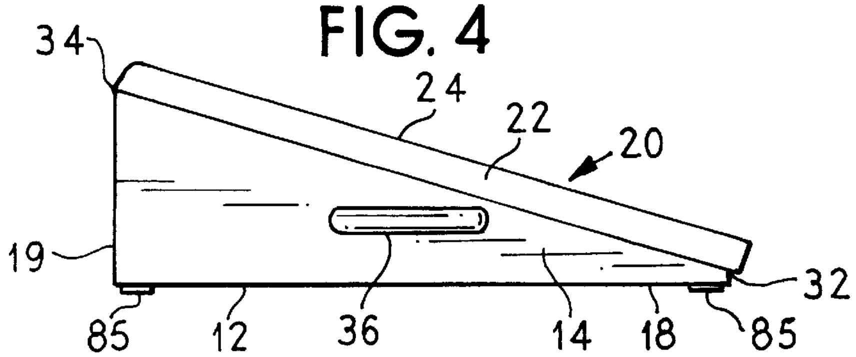
FIG. 4 is a side elevational plane view of the box seat.
Figure 5:
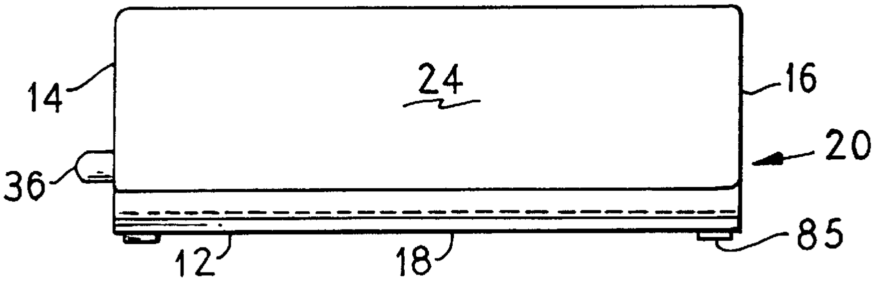
FIG. 5 is a rear elevational view of the box seat.
Figure 6:
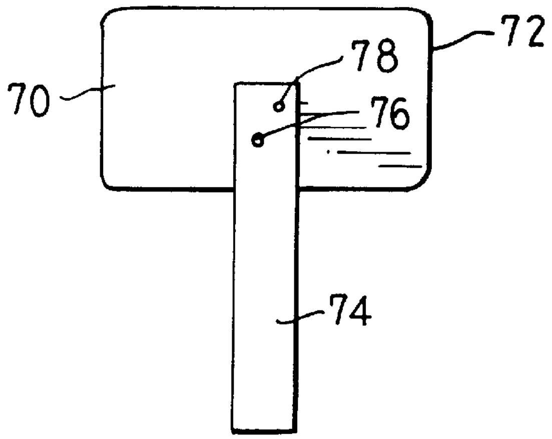
FIG. 6 is a rear elevational view of the headrest for the box seat.
Figure 7:
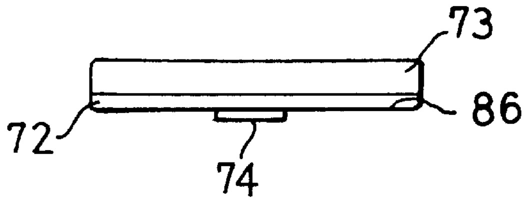
FIG. 7 is a top plan view of the headrest for the box seat.
Figure 9:
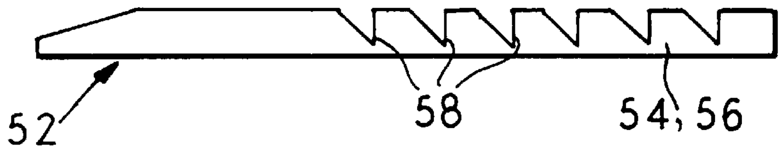
FIG. 9 is a top plan view of the support stop for the box seat.
Figure 8:
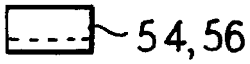
FIG. 8 is a rear elevational view of the support stop for the box seat.
Figure 10:
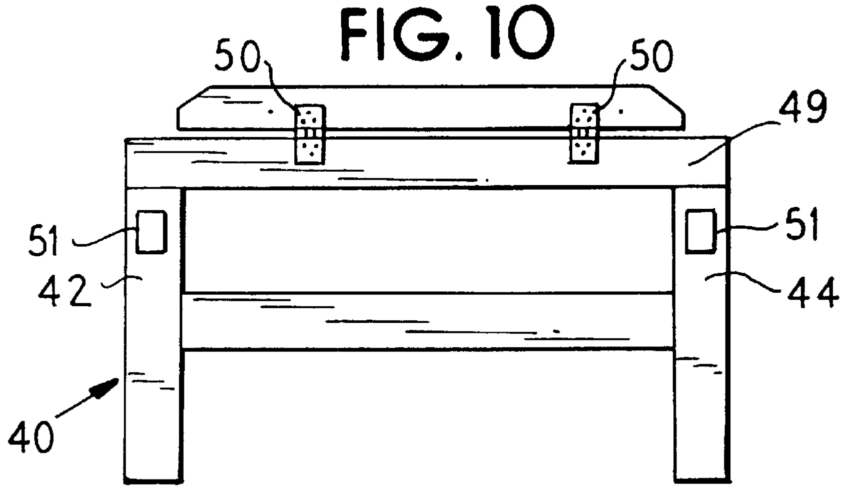
FIG. 10 is a front elevational view of the support leg for the box seat.
Figure 11:
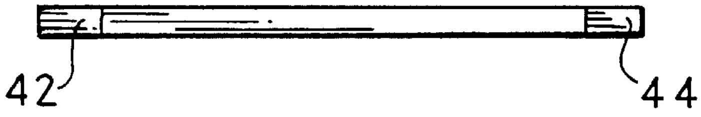
FIG. 11 is a bottom plan view of the support leg for the box seat.
Figure 15:
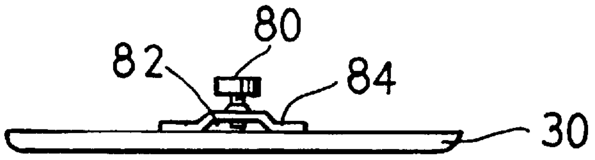
FIG. 15 is a partial sectional view showing the headrest slot.
Figure 13:
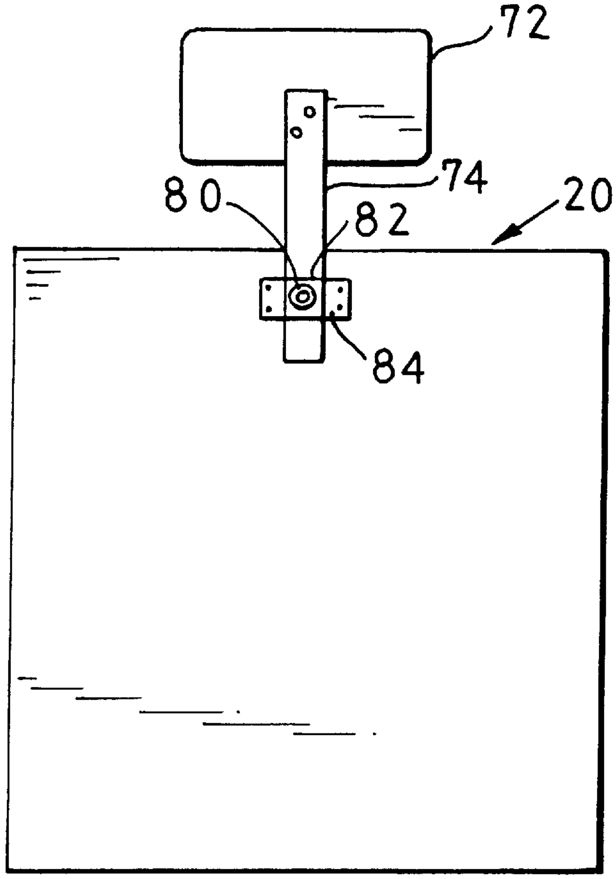
FIG. 13 is a bottom sectional view of the box seat lid/seat back unit.
Figure 12:
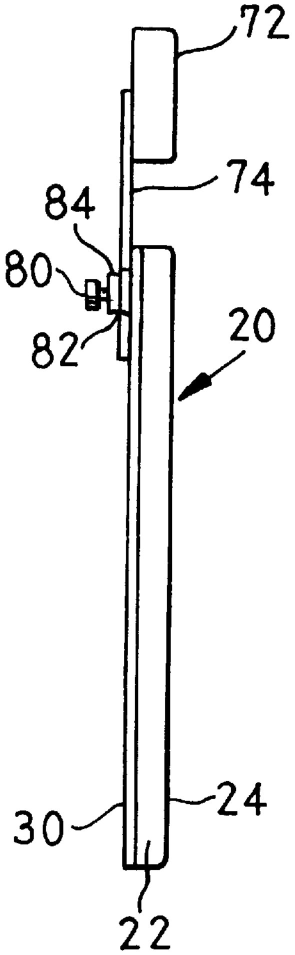
FIG. 12 is a side sectional view of the box seat lid/seat back unit.
Figure 14:
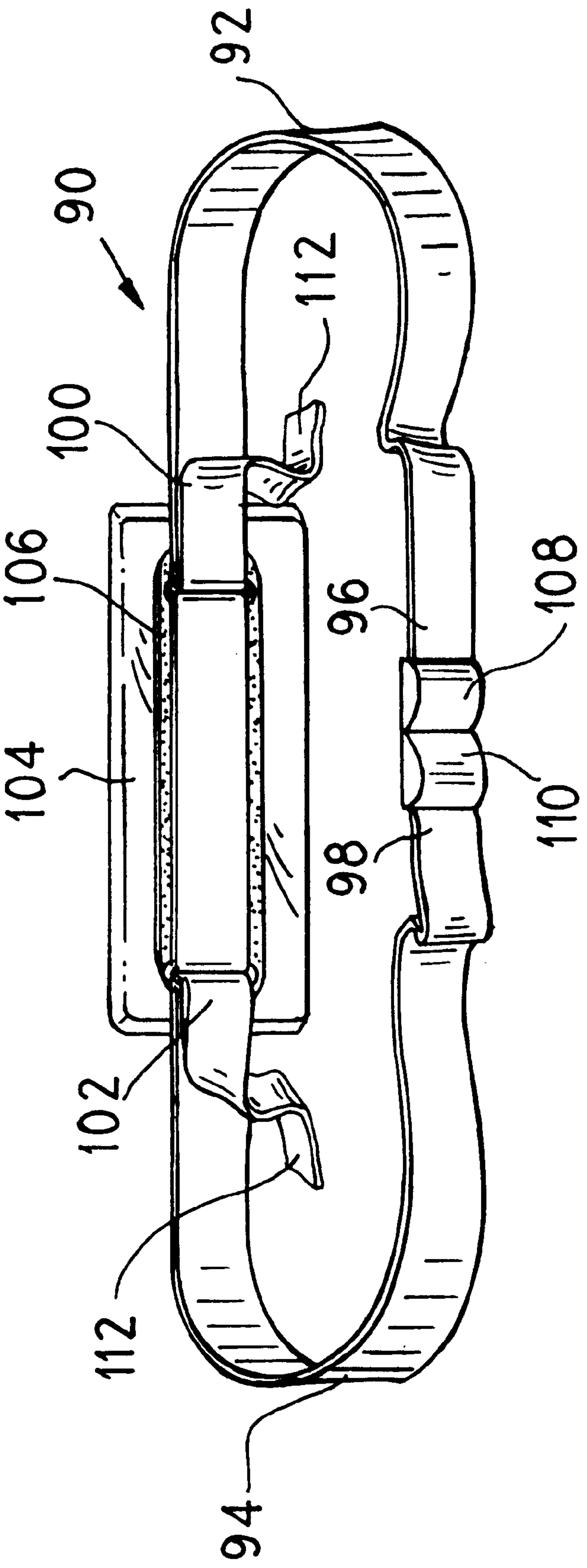
FIG. 14 is a perspective view showing an assembled chest strap and pad arrangement.

The box seat apparatus 10 utilizes a wedge or triangular shaped base 12. Base 12 may conveniently made of wood enabling economical manufacture and a pleasing natural finish. Other materials of sufficient strength, density and economy may also be used. The base 12 includes the side panels, 14, 16, the front panel 19, the bottom 18 and the lid/seat back unit 20. The lid/seat back unit 20 is covered with a one and one-half inch (1½") foam pad 22 and covered with a cover of high quality grade of upholstery sheet, 24 such as fabric or vinyl. The material sold under the trademark Rubatex is suitable. The foam pad 22, is covered with upholstery cover 24 and affixed to a substrate 30, preferably a plywood panel, however other sufficiently rigid, light, economical board could be used. A half inch (½) oak plywood panel provides good strength and economy, while having a pleasing finish for the exposed interior, which is viewable when the lid/seat back unit 20 is open.

In an alternative embodiment, rigid, or less resilient foam strips could be provided, which may be aligned at opposed edges of lid/seat back unit 20, to provide for directing the patient toward the center of the lid 20. Using strips of differing density could help center the patient, but are not necessary in the preferred embodiment.

Brass hinges 32 and locking closures 34 are used enable the opening and locking of lid 20 on box 10. A carrying handle 36, such as a suitcase handle, is attached to either front panel 19, or side panel 14 or 16 for ease in carrying.

The support mechanism 40 inside apparatus 10 provides angle adjustments for lid 20. In the preferred embodiment is constructed of wood and is designed to withstand weight and pressure. The support mechanism includes, in the preferred embodiment, a pair of legs 42, 44 pivotable from a substantially horizontal position in which the lid 20 is closed, to an angled position when the lid 20 is substantially vertical. For maximum stability, the angled position is generally equal in magnitude, but opposite the angle of the lid 20. Transverse members 46, 48 provide lateral stability to legs 42, 44. A wooden bar 49 is attached to transverse members 46, 48 and also provides for affixation of a pivoting element 50 such as a hinge, which is affixed to top or lid 20.

A support stop arrangement, generally 52, is constituted of leg engagement toothed racks 54, 56. Each rack 54, 56 has a plurality of teeth 58 formed therein. The teeth 58 receive the respective ends of legs 42, 44 in selective positions whereby the angle of top 20 is controlled. This control is accomplished by limiting the horizontal component of movement of the legs, so that based on the angle of the legs 42, 44 present relative to the top 20, angles from 20 degrees to 90 degrees of sitting, can be achieved as the legs 42, 44 are moved. While in the preferred embodiment, the legs 42, 44 engage the teeth 58, other possibilities could be utilized, such as a single rack engaging a lower transverse member, or a continuously adjustable linkage, so long as the angular adjustment is enabled with the lateral stability of the top being maintained.

A non skid surface is on the bottom 18 in all four corners. These can preferably be resilient adhesive pads squares will also be replaceable items. Three resilient feet or pegs can be affixed to end of the box seat to help with resting and standing the box seat when transporting.

A head rest 70 provides support for the head of the patient seated in the box seat apparatus 10. The head rest is made of a flat, rectangular pad constructed of a wood base with one inch (1") of foam glued to the surface and covered in a vinyl material. The pad measures eight inches (8") by five inches (5"). Mounted on the back wood side is a oblong, flat metal piece eight inches (8") in length held on by two screws. This flat metal or similar durable, light weight material can then be placed in the holding bracket located on the inside lid of the box seat. The holding bracket measures four inches (4") in width and three inches (3") in length, and is made of metal or other durable, light weight material, is flat or flush on both ends, and has a raised middle section of one-half inch (½). This raised middle section allows for the flat metal piece attached to the head rest to slide in. A knob, which is attached to the outside surface of the holding bracket, is then turned clockwise to tighten (counter clockwise to loosen) and holds the head rest in place. The length of the flat metal piece allows for the head rest to be lowered or raised. To apply the head rest, loosen the knob (counter clockwise) located on the inside of the lid. Then placing the metal ends of the head rest into the slot, tighten the knob (clockwise) until the head rest is tightly in place. This to head rest can be adjusted up and down only. A head cushion 72 preferably measures about nine inches (9") long by five and one-half inches (5½") wide and consists of a one inch (1") thick polyfoam cushion 73 affixed to a backing piece 86, preferably a one-half inch (½) thick piece of plywood. The head cushion 72 is attached to a head rest bracket 74 which is preferably composed of steel measuring one-eighth inch (⅛) thick and two inches (2") wide by thirteen inches (13") long through attachment to backing piece 86 which provides structural support.

The head cushion 72 is attached to the top of the head rest bracket 74 by two screws 76, 78 running on a diagonal. The bottom of the head rest bracket 74 slides into a slot 82 on the inside of the lid/seat back unit 20. The position of the head rest bracket 74 relative to the lid/seat back unit 20 can be adjusted within the slot 82 to suit the patient's size and comfort. A knob 80 containing a clamp 84 is located on the inside of the lid/seat back unit 20 over the slot 82, which when rotated clockwise, tightens the grip of the clamp 84 on the head rest bracket 74, allowing the patient to rest his head on the cushion 72 without fear of the head rest bracket 74 sliding down. When the unit is not in operation, the knob 80 can be rotated counter-clockwise, releasing the grip of the clamp 84 on the head rest bracket 74, allowing the head rest detail 70 to be completely removed from the lid/seat back unit 20 and stored inside the box seat apparatus 10.

The foregoing elements provide the functions of having head supports adjustable for height, lateral supports adjustable for width, pelvic straps and hip guides also adjustable for width and lumbar support with adjustable heights.

All accessories are kept in the apparatus. These items include: a lateral support strapping system; a hip guide strapping system; a removable head rest; a lumbar roll; a demonstration video; a measuring tape; a packet of treatment documentation guidelines; and a piece of non-slip material to be used under the patient.

In operation the therapist or other user will place the box seat apparatus 10 on a flat surface such as a therapy mat, the floor, or a firm bed. The bottom of the box 18 seat is the wood side with 4 squares of non-slip surface placed at each corner.

The therapist will then adjust the sitting angle from closed, at about 15 degrees to an open position between about 30 to 90 degrees. This is done by lifting the lid/seat back unit and placing the wood legs 42, 44 in the selected support stops or teeth 58. The wooden bar 49 is attached to the lid/seat back unit 20 by a hinge 50 and the wood legs 42,44 are held in place with Velcro to prevent it from falling when opening the lid/seat back unit 20. Place the legs in the appropriate support stop 52.

Prior to placing the patient on the box seat apparatus 10, it is preferred to use a piece of nonslip material (included) under the patient to prevent the patient from slipping on the mat surface covering the foam pad 22 which is attached to the lid/seat back unit 20. When the patient is in a standard bed or on the floor surface this material may not be effective.

If the patient is already positioned against the box seat 20 and it is desired to change the sitting angle, the therapist may lift the edge of lid/seat back unit 20 in an upward direction and adjust the angle. It may help to use both hands to initially raise the lid/seat back unit 20 and while holding the lid/seat back unit 20 with one hand, use the other hand to adjust the wooden bar 49. The therapist may also place two hands on the wooden bar 49 and push in an upward direction to adjust the angle.

To mount the head rest 70, the therapist may loosen the knob 80 (using typical right handed threads, in a counter clockwise direction) located on a stud or bolt threadably fitted in an aperture in slot 82. Slot 82 is in the nature of a channel mounted inside of the lid/seat back unit 20. Then placing the end of the head rest bracket 74 into the slot 82, tighten the knob 80 (clockwise) until head rest 70 is tightly in place. This head rest 70 can be adjusted up and down only.

The strap support system is constructed of six feet (6') of cloth webbing, preferably two inches (2") but possibly up to four inches (4") in width with a male and female plastic buckle fasteners to connect the two ends. Midpoint of the webbing, there is a pad measuring ten inches (10") long and six inches (6") wide.

The belt assembly 90 comprises a left belt 92 and a right belt 94. Each belt has a buckle end 96, 98 respectively, and an adjustable end 100, 102 respectively. Ends 100, 102 are constructed in an adjustable manner by affixing a fastening material, such as a hook and hoop fastener material so that they may be adjustably affixed to chest pad 104 which has a surface 106 with that portion of the fastener material (hook or loop) which complements the material at ends 100, 102. Preferably chest pad 104 can be made from 1" thick poly foam, covered with vinyl and mounted on a 2" wide webbing strap.

Male 108 and female 110 buckle connectors fixedly link ends 96, 98 while the interaction of adjustable ends 100, 102 with material 106 enables the therapists to adjust length from a location approximate the patient rather than from behind. This is an important advantage in treating patients who have difficulty sitting by a single therapist which with other devices could require two therapists.

In operation the therapist would place the front pad on the client's chest and bring the webbing to the back of the lid, fasten the ends together. The straps would be aligned about two inches (2") below the arm pit. The straps would be adjusted by affixing the free ends to the hook and loop fastener material on the pad. The use of the belt and chest pad alone is sufficient to maintain the patients hip angle at 90 degrees and help prevent extension of the lower extremities and pelvis.

An optional feature would be to attached to the webbing two plastic L-shaped pieces, one for the left side, and the other for the right side measuring four inches (4") width. One part of the L is flat measuring five inches (5") in length, and the other has a slight C curve measuring eight inches (8") in length. The curved side could be attached to the cloth webbing using a number of suitable methods, such as fitting the strap through sewn straps, the use of hook and loop fasteners, or the like. The flat side of the L could therefore be covered with hook and loop fastener material and then attached to the padded surface of the box seat. A four inch (4") wide piece of padded cloth that is eight inches (8") in length could be attached to the two ends of the plastic piece creating a triangle appearance when seen from above.

In the alternative embodiment, the lateral supports, if used, can be placed at the hips to be used as hip guides. When used in conjunction with the non slip surface, the supports of the alternative embodiment could assist with helping to maintain the patients hip angle at 90 degrees and help prevent extension of the lower extremities and pelvis. Another alternative would be to use a lumbar roll attachable at any height by attaching the two straps behind the lid, as with the alternative lateral supports.

An alternative embodiment would use auxiliary lateral pads of a nature analogous to the chest pad, which may be attached to the strap to support the patient and make more comfortable the side portion of the strap. These may be made in a manner analogous to the chest pad, or may be formed in a curved shape to conform to the patients ribs or side.

To transport the box seat apparatus 10, the therapist may close the lid/seat back unit 20 into the locked position. This will prevent the lid/seat back unit 20 from falling open during transporting. The apparatus 10 is carried by using the handle 36. The narrow end of the wedge can be placed to the front while carrying. This will help prevent the knees from being restricted from a full walking stride, another advantage to the invention.

As many and varied modifications of the subject matter of this invention will become apparent to those skilled in the art from the detailed description given hereinabove, it will be understood that the present invention is limited only as provided in the claims appended hereto.

In accordance with our invention, we claim:

1. A therapeutic apparatus comprising in combination:

a base including a bottom panel, a back panel, opposed side panels, and a front edge together defining a support and a container;

a lid pivotally mounted to the front edge of the base for movement between a closed position wherein the lid is sealed against the base and selected angled open positions wherein the lid is positioned away from the base, the lid including a front side and back side;

said side panels of said base decreasing in width from the back panel to the front edge of the base so that said lid is angled relative to the bottom panel of the base when in a closed position;

a support mechanism for supporting the lid in said selected open angled positions relative to the base including a bracket consisting of a bar pivotally mounted to the back side of the lid and two legs extending perpendicularly outwardly from the opposite ends of the bar respectively and a pair of racks mounted in the base, each of the racks including a plurality of spaced apart teeth and the legs engaging the teeth in the racks for supporting the lid in said selected open angled positions; and a strap assembly for holding a patient against the lid including a chest pad and two belts including respective first ends adjustable secured to respective ends of the chest pad and respective opposed second ends including buckles allowing the two belts to be buckled together behind the lid.

2. The apparatus of claim 1 further including a pair of generally L-shaped lateral pads associated with the strap assembly and adapted to be positioned against the sides of the patient respectively, each of the pads including a first part removably secured to each of the respective belts of the strap assembly and a second part removably secured to the front side of the lid.

3. The apparatus of claim 2 wherein the first part of each of the lateral pads is curved.

* * * * *